United States Patent [19]
Cheung et al.

[11] Patent Number: 5,898,087
[45] Date of Patent: Apr. 27, 1999

[54] ADDITION OF AMINE TO IMPROVE PARAFOMALDEHYDE

[75] Inventors: Hung-Cheun Cheung; Carolyn Supplee; George C. Seaman; H. Robert Gerberich, all of Corpus Christi, Tex.

[73] Assignee: Celanese International Corporation, Dallas, Tex.

[21] Appl. No.: 08/820,795

[22] Filed: Mar. 19, 1997

Related U.S. Application Data

[XX .
[60] Provisional application No. 60/013,766, Mar. 20, 1996.

[51] Int. Cl.$^6$ ............................ C07C 41/00; C07C 47/00; C07C 45/00
[52] U.S. Cl. ............................ 568/602; 568/422; 568/458
[58] Field of Search ................................... 568/602, 422, 568/458

[56] References Cited

U.S. PATENT DOCUMENTS

| | | | |
|---|---|---|---|
| 2,481,981 | 9/1949 | Craven | 260/340 |
| 2,519,550 | 8/1950 | Craven | 260/340 |
| 2,519,981 | 8/1950 | Richter | 223/76 |
| 2,568,016 | 9/1951 | MacLean | 260/340 |
| 2,568,018 | 9/1951 | MacLean | 260/340 |
| 2,704,765 | 4/1955 | Smithson | 568/602 |
| 2,823,237 | 2/1958 | McCants | 260/615.5 |
| 3,388,172 | 6/1968 | Dakli et al. | 568/602 |
| 3,772,392 | 11/1973 | Paleologo et al. | 260/615.5 |
| 4,550,213 | 10/1985 | Thigpen | 568/458 |

FOREIGN PATENT DOCUMENTS

| | | |
|---|---|---|
| 0 716 104 A1 | 6/1996 | European Pat. Off. . |
| 1.486.060 | 6/1967 | France . |
| 1112 505 | 8/1961 | Germany . |
| 48-8603 | 3/1973 | Japan . |
| 48-17250 | 5/1973 | Japan . |
| 869764 | 7/1961 | United Kingdom . |
| 931892 | 7/1963 | United Kingdom . |
| 1028804 | 5/1966 | United Kingdom . |

*Primary Examiner*—Paul J. Killos
*Assistant Examiner*—J. Parsa
*Attorney, Agent, or Firm*—M. Susan Spiering

[57] ABSTRACT

Disclosed is a process to produce paraformaldehyde prills having a low dissolution time and low concentration of insoluble formation. The insolubles are believed to lead to stickiness, tackiness, and loss of flowability of the product, loss of handling, and lead to storage problems of the final prill product. To address this problem, a concentrated formaldehyde solution is prepared having a purity ranging from 37%–99% and may be mixed with an amine additive, an amine and alcohol additive, or amine, alcohol, and caustic additive. Alternatively, the final prill may be sprayed with an amine or amine mixture stabilizer.

27 Claims, No Drawings

ADDITION OF AMINE TO IMPROVE PARAFOMALDEHYDE

PRIORITY CLAIM

This is a non-provisional patent application filed with the U.S. PTO on Mar. 19, 1997, claiming the benefit under 35 U.S.C. Section 119(e) of a U.S. provisional application, application Ser. No. 60/013,766 filed with the U.S. PTO on Mar. 20, 1996.

FIELD OF THE INVENTION

This invention relates broadly to the production of paraformaldehyde.

BACKGROUND OF THE INVENTION

This invention relates to the treatment of highly concentrated formaldehyde in producing solid paraformaldehyde. The technology improves the solubility and storage life of paraformaldehyde. The product is used mainly in paint and coating industries.

Paraformaldehyde is a solid form of 80% or more formaldehyde. Typically the formaldehyde concentration ranges from 90% to 96%. Paraformaldehyde is thought to be poly(oxymethylene) glycol, $HO-(CH_2O)_n-H$, with $n=8-100$. Generally, it is manufactured by concentrating an aqueous hot formaldehyde solution under reduced pressure. Upon cooling, the resulting solution solidifies. Paraformaldehyde produced by this method is generally not stable over time. Immediately after it is produced, paraformaldehyde exhibits excellent solubility in water and organic solvents such as butanol. It dissolves readily in water or alcohol by hydrolysis or depolymerization to yield free formaldehyde. However, its solubility in water and solvents decreases with time or with storage at temperatures generally greater than about 35° C. This change in solubility is presumably due to changes in the molecular weight of paraformaldehyde. To eliminate this phenomena, many stabilizers and inhibitors have been proposed. Until now, however, few have been successful in retarding the aging phenomena associated with paraformaldehyde. Generally, the degree of solubility depends largely on the degree of polymerization or the chain length of the polymer, n. So, it is desirable to control the polymerization of formaldehyde to paraformaldehyde. However, in most of the paraformaldehyde examined, not all of it dissolves in the solvent. That is, part of the paraformaldehyde remains as a solid and does not go into solution. These insolubles are believed to be poly(oxymethylene) glycol ethers. Hereafter referred to as ethers or insolubles. It is believed that these ethers affect physical properties, eg., solubility of paraformaldehyde. These ethers are formed by the reaction between paraformaldehyde and methanol in the presence of acid such as formic acid. As stated earlier, a desirable paraformaldehyde product would dissolve rapidly, produce little to no insolubles and would not continue to polymerize upon storage. It has been reported that during polymerization, formaldehyde reacts with alcohol, e.g., methanol, to form glycol ethers. This reaction is acid catalyzed. Typically formic acid exists in low concentration in the paraformaldehyde and serves as the catalyst for the reaction. These ethers are not soluble in water and hence remain as fine particulate matter upon dissolution of the paraformaldehyde. Therefore, the degree of polymerization, concentration of formic acid and methanol attribute directly to the insolubility and insolubles problems associated with paraformaldehyde. The most desirable paraformaldehyde would have a low degree of polymerization, high degree of solubility, little or no insoluble, and, most importantly, would not change with time or at storage temperatures greater than about 35° C.

Paraformaldehyde is manufactured from hot concentrated formaldehyde solutions wherein the formaldehyde varies from about 30% to about 90%, most commonly about 80% formaldehyde. Various methods exist for manufacturing the solid paraformaldehyde: (1) solidify the concentrated formaldehyde solution in a reaction vessel, with or without catalyst and mechanically break up the mass formed; (2) pour the reaction contents on to a chilled surface, e.g. conveyor belt; (3) pour reaction contents over a heated roller device; (4) utilize a prilling tower whereby concentrated formaldehyde solution is fed into a tower cooled by current of air or inert gas. These methods produce either lumps, flakes, or spherical solids (also referred to as prills). EPO-716,104 A1. Conventionally, paraformaldehyde is manufactured by vacuum evaporation of aqueous formaldehyde. For example, Sumitomo Chemical Company concentrates formaldehyde solution to 80% by weight by fractional vacuum distillation. This process, however, allows for the rapid build up of formic acid in the resulting product, Sumitomo Chemical Company, British 869,764, Jun. 7, 1961.

Previously, Celanese Corporation patented a continuous two-stage vacuum evaporation of an aqueous formaldehyde solution with a pH of about 2.9 to about 3.5, U.S. Pat. No. 2,568,016, and U.S. Pat. No. 2,568,018. In the first stage, a 60% to 80% solution is heated continuously at 45 to 70° C. under 25 to 100 mm Hg. During the second stage the formaldehyde solution is further concentrated to 80 to 90% by heating between 70 to 90° C. at 100 to 200 mm Hg. The concentrated formaldehyde is maintained at 100 to 130° C. for approximately 180 minutes. The resulting liquid is sent to a rotary flaker to produce solid chips of paraformaldehyde.

Literature has shown that the rate of formaldehyde polymerization can be controlled by the addition of catalysts. Both acids, U.S. Pat. No. 2,519,550, and German 1,112,505, and bases, U.S. Pat. No. 2,568,018 and U.S. Pat. No. 3,772,392, are said to accelerate the polymerization. Examples of the acidic catalysts are boric acid, sodium tetraborate, U.S. Pat. No. 2,519,981 and U.S. Pat. No. 2,519,550, and oxalic acid, Germanl 1,112,505.

In another effort to control the molecular weight of the paraformaldehyde, altering the drying conditions of concentrated formaldehyde has been proposed. A current of air containing either an acid or base in an amount sufficient to alter the pH of the paraformaldehyde is used in the drying process, U.S. Pat. No. 2,568,018. For instance, a treatment with triethylamine yields finely divided particles of paraformaldehyde with below 3% moisture. However, neither the molecular weight or the polymer chain length was reported to be lower.

All of these methods produce paraformaldehyde with a high molecular weight and hence, low solubility. Thereafter the paraformaldehyde becomes sticky, and difficult to flow or store. Methods are reported to make a product with high solubility, or low degree of polymerization; one is to add alcohol, generally at least 20%, such as methanol to the formaldehyde feed, DE 884,947 and U.S. Pat. No. 2,823, 237; another is to add stabilizers, such as triazine, British 1,028,804, or an aliphatic amine, diamine, tertiary amine, or hydroxylamine and sufficient base to essentially neutralize the solution to the aqueous solution of formaldehyde, GB 931,892. The addition of amine has, to date, only been reported in the production of paraformaldehyde flakes or lumps; not in the production of prills which requires different technology to produce.

The polymerization process of formaldehyde is said to continue even after the paraformaldehyde flakes or prills are formed. Therefore the molecular weight of paraformaldehyde increases during storage. This causes the desired paraformaldehyde product to lose solubility, sometimes rapidly, upon storage. Polymerization inhibitors such as hydantoins, U.S. Pat. No. 2,519,981 and U.S. Pat. No. 2,519,550, and pentaerythritol, German 1,112,505, are reported to prevent this undesirable aging process. Other reported effective inhibitors include aliphatic and cyclic amines, and amino acids, French 1,486,060 and DE 701022. Hexamine in water and solvents (methanol) have been reported to inhibit polymerization of paraformaldehyde during storage, Japanese 73/48-17,250 and 73/48-8,603.

In spite of numerous reported methods to inhibit aging effects, the art indicates the continuing need to produce paraformaldehyde which even after storage has a low dissolution time and virtually no insolubles.

SUMMARY OF THE INVENTION

This invention relates to the production of paraformaldehyde which even after considerable storage has a low dissolution time and virtually no insolubles. It has been discovered that the addition of from about 0.1. to about 1000 ppm of an amine which is relatively non-volatile at the prilling temperature of paraformaldehyde, and is soluble in aqueous formaldehyde and paraformaldehyde, to the formaldehyde at an appropriate time during the formation and prilling of the paraformaldehyde results in paraformaldehyde having low dissolution time and minimal to no insolubles. Referred amines have from about 1 to about 20 carbon atoms in the compound. The amine can be an $C_{1-20}$ aliphatic amine, an $C_{1-20}$ aliphatic diamine, a hydroxy-aliphatic amine of 1 to about 20 carbon atoms, an $C_{1-20}$ alkoxyl aliphatic amine, a primary amine, a secondary amine, a tertiary amine and the respective functionalized amines of the above, or mixtures thereof. The amine can be added neat or placed into solvents at the beginning of the paraformaldehyde production process, for example when the feed is at about 37% formalin solution. Most low molecular weight common organic solvents as well as water have been shown to be suitable, eg. water, methanol, acetone. Water is the most preferred solvent. We have found that the amine can be introduced to the hot formaldehyde liquid at or about 100° C., or at a temperature below the boiling point of the amine. Alternately, the amine can be added via a spray onto the actual paraformaldehyde prill, thereby achieving a similar effect. Amine is generally referred to herein as additive or stabilizer. Both terms are used interchangeably. Alternately, the amine can be contacted with a base, a $C_{1-20}$ aliphatic alcohol, $C_{5-15}$ aliphatic hydrocarbon or an aromatic hydrocarbon additive to improve the amine's stabilizing effects.

DETAILED DESCRIPTION OF THE INVENTION

This invention provides an improvement over prior art processes in the production of paraformaldehyde prills and results in low dissolution time and minimal to no insolubles in the product. This invention involves the use of linear and branched chain amines which contain from about 1 to about 20 carbon atoms, preferably from about six to ten carbon atoms for the production of paraformaldehyde prills.

It has been discovered that the addition of small quantities of an amine compound serve to inhibit polymerization in paraformaldehyde prills. Inhibiting polymerization results in paraformaldehyde prill product, having a dry, non-tacky surface which is desired for ease in handling and storage.

It has generally been found that too much amine produces prills which are sticky and difficult to handle and transport. Additionally, large quantities of amine may be considered an impurity in the product. Yet, too small an amount of amine, results in no effects being observed. Therefore a sufficient amount of amine to produce the polymerization inhibiting result is desired. The amount of amine necessary is generally dependent upon the % concentration of formaldehyde beginning with eg., 37% HCHO—~100 ppm amine, 87% HCHO—~250 ppm amine.

Thigpen (U.S. Pat. No. 4,550,213) and Derivados (EP 0716104 A1) references disclose use of paraformaldehyde formulations which include amines, together with an acid or base catalyst. These references do not disclose recognition of the problem of tackiness or stickiness of prills and subsequent difficulty in flowability during handling and storage. Although the art mentions use of amines as catalysts, it does not recognize the use of amines in the absence of an acid or basic catalyst in the production of paraformaldehyde prills to inhibit aging difficulties.

An embodiment of the present invention therefore relates to a process for the manufacture of paraformaldehyde prills comprising.

a) providing a formaldehyde solution of at least 37% formaldehyde and contacting the formaldehyde solution with an amine stabilizer;

b) heating the mixture of step (a) to a temperature ranging from about 70° C. to about 130° C.

c) aging the mixture for a sufficient amount of time to polymerize the formaldehyde mixture and form paraformaldehyde;

d) transferring the paraformaldehyde through a nozzle to form prills which fall into a countercurrent flow of gas in a tower to further polymerize and solidify.

After solidification, the prills are transferred into a separate quenching vessel wherein the prills further polymerize and dry.

Suitable amine compounds comprise a primary, secondary, or tertiary amine, cyclic amine, diamine, or alkanol amine. Exemplary amines include methylamine, ethyl amine, n-propylamine, n-butylamine, iso-butylamine, tertbutylamine, dimethyl amine, diethylamine, di-n-propylamine, di-iso-propylamine, and dibutylamine, triethylamine and triethanolamine, hexamethylenetetramine (hexamine or HMTA), 2-ethylhexylamine ,(EHA), 2-aminopropanediol, hexylamine (HA), ethanolamine, mixed C-20 amine, mixed C-10 amine, cyclohexylamine, 1,2 dimethoxypropane amine, triethylamine, ethanolamine, 2-amino-1,3-propanediol, 1-amino-pentane, 2-methyloxypropylamine. "Mixed" refers to a mixture of branched and linear amine compounds.

Experimentation indicated a mixture of the identified amines with a small amount of caustic (NaOH) yielded an improvement in percent insolubles of the final paraformaldehyde product. A preferred amount of caustic includes about 100 ppm caustic mixed with amine. The range of caustic as a mixture with amine can be from about 0.01 to about 1% based on the concentration of the concentrated formaldehyde solution.

It was found that not all amines performed the same to yield improvement in the stability of the concentrated formaldehyde (wherein the concentration ranges from about 60–87%). Amines which increased the solubility of the paraformaldehyde by approximately a factor of two(2) included ethanolamine, n-propylamine, 2-ethyl hexyl amine, hexamine, diaminopentane and HA. All these amines have been shown to keep the solubility of the paraformaldehyde on the order of 70% even upon storage at ambient storage temperatures for extended periods of time. In concentrated formaldehyde samples containing these amine, insolubles were found to be reduced by approximately half compared to concentrated formaldehyde without these amines or stabilizers. It was found that, although a reduction in insolubles was observed, amines with long chains, branched amines, and some tertiary amines had a weak effect on the reduction of insolubles in samples of concentrated formaldehyde.

It is preferred that the amine be present in a concentration of about 0.1 to about 1000 ppm, preferably about 150–400 ppm and most preferably about 200–300 ppm. It may be contacted directly with the concentrated formaldehyde before prills are formed, or sprayed onto the paraformaldehyde prills. The amine may be introduced directly into concentrated formaldehyde, eg., 80–89% paraformaldehyde, or 37% formaldehyde. The art had disclosed use of an amine, however, the general procedure of the art involves producing paraformaldehyde by cooling the concentrated formaldehyde solution with a polymerization regulator or by drying the concentrated paraformaldehyde powder with an amine. (U.S. Pat. No. 2,568,018; U.S. Pat. No. 3,772,392). Additionally, the art disclosed use of amine in production of paraformaldehyde flakes, not prills. The present invention contacts the amine directly with the concentrated formaldehyde, thus eliminating the need for paraformaldehyde powder and or cooling the solution. Laboratory results indicated that the preferable concentration of the additive is about 200–300 ppm, depending on the amine of choice.

An embodiment of the present invention involves contacting amine and hot concentrated formaldehyde. It has been found that about 87% concentrated hot formaldehyde works well to combine with the amine additive. Once the amine is mixed with the formaldehyde, it is transferred to a nozzle where the formaldehyde mixture is transferred or dropped through a tower to form prills. The tower is maintained with a countercurrent of air or inert gas (such as nitrogen). The prills formed drop to the bottom of the tower and are directed to a quenching vessel.

An alternate embodiment of the present invention involves forming an amine stabilizer mixture wherein the amine is mixed or contacted with a lower alkane alcohol, eg. $C_{1-4}$, preferably methanol. The alcohol may be added to the amine and hot formaldehyde liquid. The alcohol additive was found to aid in stabilizing the paraformaldehyde product. Use of methanol is disclosed in the formaldehyde formulations of the art, however only in concentration ranges above 4% based on the formaldehyde feed. It is preferred to add the alcohol additive to the amine at a range of less than 4%, preferably less than 2%. Alternately the amine can be mixed with a base such as NaOH, again the total additive is <4%. Additional additives include $C_{1-20}$ aliphatic alcohol, $C_{5-15}$ aliphatic hydrocarbon, aromatic hydrocarbon, or a base additive, and exemplary additives include cyclohexane, acetone, methyl ethyl ketone, sodium hydroxide, ethanol, methanol, butanol, ethyl acetate, butyl acetate and the like.

An alternate embodiment of the present invention relates to a process for the manufacture of paraformaldehyde comprising:

a) providing a formaldehyde solution of at least 37%;
b) heating the mixture- of step (a) to a temperature ranging from about 70° C. to about 130° C.;
c) aging the mixture for a sufficient amount of time to polymerize the formaldehyde mixture and form paraformaldehyde;
d) transferring the paraformaldehyde through a nozzle to form prills which fall into a countercurrent flow of gas in a tower to further polymerize and solidify.

Generally the prills are then transferred into a separate quenching vessel wherein the prills further polymerize and dry at from about ambient temperature to about 300° C., for from about 1 to about 20 hours, preferably from about 2 to about 9 hours. Thereafter they are contacted with an amine stabilizer which is sprayed onto the prills.

The spraying of the prills occurs by conventional procedure spraying amine solution to 'cold' solid prills so as to coat the amine. Generally, the amine solution is dissolved in a common organic, volatile solvent such as a $C_{1-20}$ aliphatic alcohol, $C_{5-15}$ aliphatic hydrocarbon, aromatic hydrocarbon, or a base. Exemplary solvents include methanol, butanol, ethanol, methyl ethyl ketone, acetone, cyclohexane, ethyl acetate, butyl acetate, and the like.

The heating process associated with the mixture of amine and formaldehyde is generally conducted at a temperature ranging from about 70° C. to about 130° C., preferably from about 80° C. to about 100° C. The mixture is typically aged (prior to transfer through a nozzle) for a time of about 0.1 to about 3 hours, preferably about 20 to about 40 minutes, and most preferably about 20 to about 30 minutes.

EXAMPLES

Laboratory samples were prepared for investigation. The comparison of the amine additives was accomplished by combining the amine and the hot, highly concentrated formaldehyde. The amount of amine added to the formaldehyde varied from about 10–1000 ppm. Laboratory results indicated that the preferable concentration of the additive to be between 200–300 ppm, depending on the amine of choice. In order to assure that polymerization reaction had been stopped, the mixture of amine and formaldehyde was cooled to −52° C. The solid solution was then ground to a fine powder prior to testing. All samples were stored at a range of temperature from about 25° C.–70° C. for a six month period. For storage life evaluations the samples were maintained between 35–40° C. for a five week period. The data suggests that the five week storage at elevated temperature approximates storage of the actual paraformaldehyde product for one year at room temperature. After storing the samples for five weeks, the samples were tested for solubility, insolubles, resorcinol reactivity, average molecular weight, methanol, acid, as well as other physical properties.

EXAMPLE 1

Paraformaldehyde was manufactured substantially similar to that disclosed in U.S. Pat. Nos. 2,568,016, 2,568,017, 2,568,018. An aqueous solution of 37% formaldehyde was concentrated through sequential vacuum evaporation. The solid product contained either 91% or 95% formaldehyde. To observe the effect of additives, 86% to 89% formaldehyde at the last stage of evaporation was used, Approximately, 500 grams of the resulting 86% solution was collected from the manufacturing unit of paraformaldehyde. The solution was maintained above 60° C. 0.05 gram of the amine or 100 part per million (ppm) was immediately added to the formaldehyde solution with thorough mixing. The solution was then frozen in dry ice to a temperature of about −56° C. for transportation. Upon cooling the solution solidified to paraformaldehyde. The resultant solid was then ground into a fine powder of 500 to 700 microns in the laboratory. The powder was analyzed for amine, formaldehyde, methanol and water concentrations, average molecular weight, solubility, insolubles and resorcinol reactivity. Micro-coudlometry was used to determine the amount of nitrogen and amine in the sample.

By following the above procedures, various additives were evaluated in an attempt to modify the solubility of paraformaldehyde. Results of testing after storage for 35 days at 35° C. are given in Table 1.

TABLE 1

Storage test of paraformaldehyde with additives of 100 ppm at 35° C. for 35 days

| | | 0 days at 35° C. | | 35 days at 35° C. | |
|---|---|---|---|---|---|
| Additives (100 ppm) | Amine detected | Solubility (%) | Insolubles (ppm) | Solubility (%) | Insolubles (ppm) |
| Hexa-methylene-tetramine | 85 | 100 | 33 | 65 | 65 |
| Ethanolamine | 70 | 100 | 17 | 60 | 85 |
| 2-Ethylhexyl-amine | 87 | 100 | 0 | 57 | 100 |
| normal Propyl-amine | 100 | 96 | 30 | 51 | 51 |
| Hexylamine | 75 | 100 | 17 | 48 | 132 |
| Hexa-methylene-diamine | 95 | 89 | 20 | 34 | 34 |
| Mixed C-20 amine | 98 | 85 | 67 | 35 | 100 |
| 56% Methanol, 22% Formaldehyde | 0 | 77 | 33 | 28 | 245 |
| 12% Methanol, 27% Formaldehyde | 0 | 22 | 148 | 15 | 196 |
| iso-propylamine | 56 | 89 | 65 | 30 | 67 |
| Hexylamine, 10 ppm | <10 | 91 | 17 | 0 | 119 |
| Mixed C-10 amine | 65 | 82 | 49 | 0 | 138 |
| Formaldehyde without additives | 0 | 76 | 54 | 35 | 213 |

EXAMPLE 2

Using the procedure of Example 1, five amine additives were evaluated. The amount of each additive was 100 part per million (ppm). Additives evaluated included hexylamine, cyclohexylamine, 1,2-dimethoxypropane, triethylamine and hexanediol. Samples with the additives were stored in an oven at 35° C. for five weeks. Results were summarized in Table 2. Among chemicals tested, amines gave the best results. Various amines including linear, branched, alkyl, aromatic as well as short and long chain amines were evaluated. Poor results were obtained for short chain tertiary amines that were branched. In contrast, longer chain primary and secondary amines produced more desirable results with comparable solubility.

As seen in Table 2, hexylamine, even after storage for five weeks at 35° C., resulted in 96% of the sample being dissolved in water. Without the amine, 40% of paraformaldehyde was soluble in water. Originally, the solubility of paraformaldehyde before storage was 97%.

Besides primary amine, it was found that secondary amines and diamines enhance solubility. In contrast, cyclic tertiary amines and diols yielded poor results.

TABLE 2

| Additives | 0 days at 35° C. | 35 days at 35° C. |
|---|---|---|
| Formaldehyde without additives | 97% | 40% |
| Hexylamine | 100% | 96% |
| Cyclohexylamine | 95% | 76% |
| 1,2-Dimethoxypropane | 99% | 47% |
| Triethylamine | 97% | 44% |
| Hexanediol | 74% | 36% |

EXAMPLE 3

Using the procedure of Example 1, four additives were evaluated. The concentration of additives was 100 ppm. Samples were stored at 35° C. for 15 days. Solubility of samples for the storage test is given in Table 3. Additives included hexylamine, diaminopentane, sodium hydroxide, and hexanediol. Both hexylamine and diaminopentane yielded 98% of the sample dissolving in water, even after storage. Without additive, paraformaldehyde had a solubility of 21%.

The present results confirm the superior performance of hexylamine as mentioned in Example 2. Hexylamine and diaminopentane improve the solubility of paraformaldehyde. In contrast, sodium hydroxide, and hexanediol yielded weak results after 15 days at 35° C.

TABLE 3

| Additives | 0 days at 35° C. | 15 days at 35° C. |
|---|---|---|
| Formaldehyde without additives | 56% | 21% |
| Hexylamine | 100% | 98% |
| Diaminopentane | 99% | 98% |
| Hexanediol | 51% | 17% |
| Sodium hydroxide | 52% | 33% |

EXAMPLE 4

Procedure of Example 1 was repeated using 400 ppm of amines. Amines included hexamethylenetetramine, 2-ethylhexylamine, 2-amino-propanediol and hexylamine. After five weeks of storage at 35° C., these amine sustained a solubility to 62% to 68%. Insolubles ranged from 50 to 100 ppm. Results are depicted in Table 4. Similar to Example 3, hexylamine was found to perform well. Additionally, hexamethylenetetramine, 2-ethylhexylamine, and 2-aminopropanediol also increased solubility significantly.

TABLE 4

| Types of amines | Amine | 0 days at 35° C. | | 35 days at 35° C. | |
|---|---|---|---|---|---|
| (400 ppm added) | detected (ppm) | Solubility (%) | Insolubles (ppm) | Solubility (%) | Insolubles (ppm) |
| Hexamethylene-tetramine | 280 | 99 | 60 | 68 | 50 |
| 2-Ethylhexyl-amine | 323 | 100 | 17 | 63 | 81 |

TABLE 4-continued

| Types of amines (400 ppm added) | Amine detected (ppm) | 0 days at 35° C. | | 35 days at 35° C. | |
|---|---|---|---|---|---|
| | | Solubility (%) | Insolubles (ppm) | Solubility (%) | Insolubles (ppm) |
| 2-amino-propanediol | 360 | 100 | 0 | 62 | 83 |
| Hexylamine | 350 | 100 | 0 | 64 | 100 |
| Formaldehyde without additives | 0 | 100 | 33 | 35 | 213 |

EXAMPLE 5

The procedure of Example 1 was repeated using 1000 ppm amine. The amines included hexamethylenetetramine, 2-ethylhexylamine, ethanolamine, hexylamine and methoxypropylamine. After five weeks of storage at 35° C., all amines except methoxypropylamine improved solubility to 70–85% and kept insolubles to less than 100 ppm. Results are depicted in Table 5.

TABLE 5

| Types of amines (1000 ppm added) | Amine detected (ppm) | 0 days at 35° C. | | 35 days at 35° C. | |
|---|---|---|---|---|---|
| | | Solubility (%) | Insolubles (ppm) | Solubility (%) | Insolubles (ppm) |
| Hexamethylene-tetramine | 800 | 99 | 33 | 85 | 60 |
| 2-Ethylhexyl-amine | 790 | 100 | 17 | 78 | 83 |
| Hexylamine | 1290 | 100 | 33 | 72 | 67 |
| Ethanolamine | 750 | 100 | 17 | 80 | 17 |
| Formaldehyde without additives | 0 | 76 | 54 | 35 | 213 |
| 2-Methoxy-propyl-amine | 1000 | 100 | 0 | 56 | 0 |

Properties of the paraformaldehyde changed when amine additive was added. Results were listed in Table 6. For instance, 2-ethylhexylamine and hexamethylenetetramine enhanced the solubility of paraformaldehyde by reducing the average molecular weight.

TABLE 6

Properties of paraformaldehyde with additives at day 0 of the storage test.

| Additives | Resorcinol Reactivity (sec) | Averaged mol wt (g/mol) | Averaged chain length | Solubility (%) | Insolubles (ppm) |
|---|---|---|---|---|---|
| 2-ethylhexylamine | 82 | 164 | 4.9 | 100 | 33 |
| Hexamethylene-tetramine | 109 | 166 | 4.9 | 100 | 0 |
| n-Hexylamine | 97 | 175 | 5.2 | 100 | 17 |
| Paraformaldehyde without additives | 126 | 167 | 5.0 | 76 | 54 |

EXAMPLE 6

Besides types of amine, it was found that the amount of amine affected both solubility and insolubles. Following the procedure of Example 1, a storage test was conducted on paraformaldehyde having hexylamine from 10 to 1000 ppm. Data in Table 7 indicates that hexylamine improves the paraformaldehyde significantly. With 1000 ppm hexylamine, the product still retained 100% solubility and 130 ppm after 35 days of testing.

TABLE 7

Effect of hexylamine on Paraformaldehyde.

| Amounts of hexyl-amine (ppm) | 0 days at 35° C. | | 35 days at 35° C. | |
|---|---|---|---|---|
| | Solubility (%) | Insolubles (ppm) | Solubility (%) | Insolubles (ppm) |
| 10 | 91 | 17 | 0 | 119 |
| 50 | 95 | 25 | 48 | 119 |
| 100 | 100 | 0 | 34 | 132 |
| 500 | 100 | 0 | 64 | 100 |
| 1000 | 100 | 33 | 85 | 67 |

EXAMPLE 7

The procedure of Example 1 was repeated using samples containing 2-ethylhexylamine at up to 1000 ppm. Results from Tables 8 and 9 indicate that ethylhexylamine increases the product's solubility and decrease of insolubles. The increase in solubility corresponds to a decrease of molecular weight. After 14 days at 40° C., the sample with 150 ppm of 2-ethylhexylamine had 85% solubility and 63 ppm insolubles. Its average molecular weight was 181 g/mole. Without the amine, the sample had 62% solubility and 83 ppm. The average molecular weight of the aged sample was 192 g/mole.

TABLE 8

Storage of Paraformaldehyde with Ethylhexylamine for two weeks at 40° C.

| Amounts of Ethylhexyl-amine added | Solubility (%) | | Insolubles (ppm) | | Averaged mol wt (g/mole) | |
|---|---|---|---|---|---|---|
| | 0 Day | 14 Days | 0 Day | 14 Days | 0 Day | 14 Days |
| 0 | 92 | 62 | 60 | 83 | 167 | 192 |
| 100 | 99 | 76 | 33 | 17 | 161 | 181 |
| 150 | 99 | 87 | 83 | 63 | 162 | 181 |
| 300 | 99 | 88 | 67 | 50 | 159 | 186 |
| 500 | 100 | 89 | 17 | 50 | 154 | 150 |

TABLE 9

Storage of Paraformaldehyde with Ethylhexylamine for five weeks at 40° C.

| Amine added | Amine detected | Solubility (%) | | Insolubles (ppm) | | Averaged mol wt (g/mole) | |
|---|---|---|---|---|---|---|---|
| | | 0 Day | 35 Days | 0 Day | 35 Days | 0 Day | 35 Days |
| 0 | 0 | 92 | 35 | 54 | 221 | 167 | 213 |
| 100 | 79 | 99 | 53 | 33 | 68 | 161 | 180 |
| 150 | 87 | 99 | 57 | 83 | 70 | 162 | 205 |
| 300 | 210 | 99 | 60 | 67 | 92 | 159 | 177 |
| 500 | 323 | 100 | 63 | 17 | 81 | 154 | 166 |
| 1000 | 790 | 100 | 78 | 17 | 130 | 154 | 160 |

EXAMPLE 8

Paraformaldehyde prill samples were manufactured similar to that disclosed in U.S. Pat. No. 2,566,016, U.S. Pat. No. 2,566,017, U.S. Pat. No. 2,566,018. An aqueous solution of 37% formaldehyde was concentrated through sequential vacuum evaporation and then transferred through a nozzle to produce a prill. The solid product contained between 91–95% formaldehyde. Typically, about 100–200 ppm amine was added to the concentrated formaldehyde solution before transferring the paraformaldehyde through a nozzle to form prills which fall into a countercurrent flow of gas in a tower to polymerize and solidify. Typically, 500 grams of the resulting 91–95% paraformaldehyde prills were collected from the manufacturing unit of paraformaldehyde. Paraformaldehyde prills were made with and without caustic (NaOH). The paraformaldehyde prills were then stored at 0° C. until ready for analysis. The prills were analyzed for amine, formaldehyde, methanol and water concentrations, average molecular weight, solubility and insolubles and resorcinol reactivity. Micro-coulometry was used to determine the amount of nitrogen ad amine in the sample. Results of testing after storage for 35 days at 35° C. are given in Table 10 and 11.

Without caustic present the amine tested increased the solubility of the paraformaldehyde and reduced the insolubles. At the caustic and amine levels tested, the paraformaldehyde prills exhibited a slight solubility improvement and again a reduction of insolubles.

TABLE 10

(with Amine Stabilizer)

| Paraformaldehyde Prill Samples | Amine detected | 0 days at 35° C. | | 35 days at 35° C. | |
|---|---|---|---|---|---|
| | | Solubility (%) | Insolubles (ppm) | Solubility (wt %) | Insolubles (ppm) |
| 91% | 0 | 71 | 83 | 7 | 333 |
| Sample 1 | 167 | 89 | 17 | 46 | 33 |
| Sample 2 | 176 | 89 | 34 | 37 | 42 |
| Sample 3 | 170 | 91 | 50 | 29 | 40 |
| Sample 4 | 178 | 98 | 17 | 33 | 50 |
| Sample 5 | 173 | 98 | 33 | 62 | 50 |
| 95% | 0 | 46 | 350 | 25 | 832 |
| Sample 6 | 109 | 91 | 42 | 44 | 20 |
| Sample 7 | 84 | 90 | 33 | 50 | 66 |
| Sample 8 | 93 | 89 | 17 | 23 | 33 |

TABLE 11 with Amine + NaOH stabilizer mixture

| Paraformaldehyde Prill Samples | Amine detected | Sodium detected | 0 days at 35° C. | | 35 days at 35° C. | |
|---|---|---|---|---|---|---|
| | | | Solubility (wt %) | Insolubles (ppm) | Solubility (wt %) | Insolubles (ppm) |
| 91% | 0 | 1.275 | 71 | 83 | 7 | 333 |
| *C.F., 87% | 183 | 0.924 | 73 | 166 | 43 | 33 |
| Sample 1 | 107 | 0.848 | 81 | 17 | 33 | 17 |
| Sample 2 | 119 | 0.887 | 86 | 17 | 24 | 0 |
| Sample 3 | 119 | 0.906 | 87 | 33 | 25 | 9 |
| Sample 4 | 106 | 0.824 | 87 | 17 | 28 | 17 |
| 95% | 0 | 0.996 | 46 | 350 | 25 | 832 |
| Sample 5 | 46 | 0.599 | 87 | 17 | 17 | 25 |
| Sample 6 | 38 | 0.589 | 90 | 9 | 21 | 42 |
| Sample 7 | 27 | 0.37 | 87 | 41 | 41 | 17 |

*C.F. = Concentrated formaldehyde

EXAMPLE 9

Using the procedure of Example 1, a combination of 200 ppm 2-ethylhexylamine and 0.2 ppm of sodium hydroxide was added to the formaldehyde solution. Samples were stored at 40° C. for two weeks. After the test period, samples with amine or with a mixture of amine and sodium hydroxide yielded solubility values of about 75% to 83%. Both samples reduced insolubles to about 100 ppm. In contrast, the original sample without additives had 173 ppm insolubles and 41% solubility.

TABLE 12

| Samples | Solubility (%) 0 Day | Solubility (%) 14 Days | Insolubles (ppm) 0 Day | Insolubles (ppm) 14 Days | Averaged mol wt (g/mole) 0 Day | Averaged mol wt (g/mole) 14 Days |
|---|---|---|---|---|---|---|
| Paraformaldehyde without additives | 92 | 41 | 116 | 173 | 163 | 200 |
| +200 ppm EHA | 98 | 83 | 17 | 83 | 161 | 161 |
| +200 ppm EHA + 0.2 ppm NaOH | 99 | 75 | 33 | 100 | 161 | 172 |
| +1 ppm NaOH | 90 | 52 | 50 | 110 | 150 | — |
| +10 ppm NaOH | 68 | 12 | 0 | 86 | 170 | — |

To understand the formation of insolubles, the insolubles were isolated and identified. The insolubles were found to be oxymethylene glycol ether with an average chain length of eight. Many analytical techniques were employed to characterize the insolubles. Techniques included solid state nuclear magnetic resonance, head space gas chromatography, mass spectroscopy, differential scanning calorimetry and infrared spectroscopy.

Solubility Test

To determine the solubility of paraformaldehyde, a gravimetric method was used. The method involves dissolving 10% of paraformaldehyde in water at 70° C. for fifteen minutes. Solubility is determined by weighing the portion of product that is not soluble after the test. Solid paraformaldehyde samples were ground to 400–700 microns by using a Micro-Miller grinder. The paraformaldehyde and 90±0.01 grams of deionized and distilled water were placed into a round bottom flask equipped with a condenser. The flask was placed a constant temperature bath. When the temperature of the solution reached 70° C., 10±0.01 grams of paraformaldehyde were added into the solution. The mixture was stirred vigorously at 200 rpm for fifteen minutes. Periodically, the sides of the flask were rinsed with the supernatant to ensure all solids were submerged in the solution. The mixture was filtered hot. The 0.45 micron, Teflon filter from Micron Separations Incorporated was utilized. The filtrate was washed with 50 grams of cold water and the solid dried for one hour at room temperature under a vacuum of about 200 mm Hg. The filtrate was sparged with dry nitrogen at room temperature. The insolubles were weighed and analyzed for formaldehyde content and molecular weight. The solubility was calculated accordingly:

$$\% \text{ Solubility} = [1-(\text{Weight of filtrate})/\{(\text{weight of paraformaldehyde})*\text{assay of formaldehyde}\}] * 100\%$$

For instance, in one experiment, 10.1145 grams of paraformaldehyde obtained from the fourth stage evaporator were dissolved in 90.1950 grams of water. After fifteen minutes, the solubility was 76%.

$$\% \text{ Solubility} = [1-\{(2.4975-0.0936)/10.114\}]*100 = (100-23.76) = 76.2\%$$

This method compared favorably and yielded similar results to another method using titration of sodium sulfite and sulfuric acid. For the example listed above, the solubility by titration was determined to be 78.5%.

Insolubles Test

This method uses weight to determine the amount of insoluble polymer in paraformaldehyde with pH adjustment. Therefore, caution is taken to prevent any contamination by small particles such as dust and other air-born particles. Drying conditions such as temperature and time are also critical to the consistency of the test. The solid paraformaldehyde sample was ground to 400–700 microns by using a Micro-Miller grinder. The sample was covered and set aside. The samples were dried in a vacuum oven at about 70° C. for 20 minutes. The 0.45 micron, Teflon filter utilized was from Micron Separations Incorporated. The dried filter was stored in a desiccator and tare weight obtained of the dried filter. The tared, dried filter was inserted in the Millipore filter. 24 grams of a pH 9 buffer solution was heated to reflux about 100° C. in a 250 round bottom flask. A pH/9 Fisher Scientific buffer, #SR114–20, is a 0.1 molar solution of boric acid, potassium chloride, sodium hydroxide. 6±0.01 grams of paraformaldehyde was added into the round bottom flask, equipped with a condenser. The solution was heated to reflux, about 100° C. and stirred at 150 rpm. The sides of the flask were rinsed with the supernatant periodically to ensure all solids were submerged in the solution. Remove and filter the mixture hot. The filtrate was washed with 50 grams of water and then 50 grams of reagent graded acetone. The solid was dried for one hour at room temperature under a vacuum of about 200 mm Hg. The filtrate was sparged with dry nitrogen at ambient temperature. The insolubles were weighed and analyzed for its formaldehyde content and molecular weight. The weight of the insolubles was recorded in part per millions.

For instance, a 5.8926 grams of powdered paraformaldehyde was dissolved in 24.0325 grams of buffer solution. After one hour, 0.0010 grams were recovered. That is, the sample contained 170 part per million (ppm). 1% equals to 10,000 ppm.

$$\text{Insolubles} = 0.0010/5.8929 = 0.01697\% = 170 \text{ ppm}$$

Average Molecular Weight

The average molecular weight of paraformaldehyde was obtained by determining total and free water in accordance with that disclosed in U.S. Pat. No. 3,772,392.

Resorcinol Reactivity

Resorcinol reactivity was determined by methods well known in the art, eg. U.S. Pat. No. 2,519,550 and U.S. Pat. No. 2,519,981.

Concentration of Formaldehyde:

The titration procedures employed were are described in the test to determine formaldehyde content per A.S.T.M. Method D 2194-84.

What is claimed is:

1. A process for the manufacture of paraformaldehyde comprising:
   a) providing a formaldehyde solution essentially absent of acid or basic catalyst and of a least 37% formaldehyde and contacting the formaldehyde solution with an amine stabilizer;
   b) heating the mixture of step (a) to a temperature ranging from about 70° C. to about 130° C.;
   c) aging the mixture for a sufficient amount of time to polymerize the formaldehyde mixture and form paraformaldehyde;

d) transferring the paraformaldehyde through a nozzle to form prills which fall into a countercurrent flow of gas in a tower to further polymerize and solidify.

2. The process of claim 1 wherein the amine comprises a primary, secondary, or tertiary amine, cyclic amine, diamine, $C_{1-20}$ aliphatic, $C_{2-20}$ alkoxy amine, hydroxyamine, the respective functionalized amines of the above, and mixtures thereof.

3. The process of claim 2 wherein the amine consists essentially of methylamine, ethyl amine, n-propylamine, n-butylamine, iso-butylamine, tertbutylamine, dimethyl amine diethylamine, di-n-propylamine, di-iso-propylamine, and dibutylamine, triethylamine and triethanolamine, hexamethylenetetramine, 2-ethylhexylamine, 2-aminopropanediol, hexylamine, ethanolamine, mixed $C_{20}$ amine, mixed $Cl_0$ amine, cyclohexylamine, 1,2 dimethoxypropane amine, triethylamine, ethanolamine, 1-amino-1,3-propanediol, 1-aminopentane, and 2-methyloxypropylamine.

4. The process of claim 1 wherein the amine is present in a concentration of from about 0.1 to about 1000 ppm.

5. The process of claim 4 wherein the amine is present in concentration of about 150 to about 400 ppm.

6. The process of claim 5 wherein the amine is present in concentration of about 200 to about 300 ppm.

7. The process of claim 1 wherein the aging step (c) is about 0.1–3 hours.

8. The process of claim 7 wherein the aging step is about 20–40 min.

9. The process of claim 8 wherein the aging step is about 20–30 min.

10. The process of claim 1 wherein the heating temperature of step (b) is about 80° C. to about 120° C.

11. The process of claim 10 wherein the heating temperature for step (b) is about 80° C. to about 100° C.

12. A process for the manufacture of paraformaldehyde comprising:
    a) providing a formaldehyde solution of at least 37% formaldehyde;
    b) heating the mixture of step (a) to a temperature ranging from about 70° C. to about 130° C.;
    c) aging the mixture for a sufficient amount of time to polymerize the formaldehyde mixture and form paraformaldehyde;
    d) transferring the paraformaldehyde through a nozzle to form prills which fall into a countercurrent flow of gas in a tower to further polymerize and solidify;
    e) and contacting the paraformaldehyde prills by spraying with an amine stabilizer.

13. The process of claim 12 wherein the prills of step (d) further polymerize and dry at from about ambient temperature to about 300° C. for from about 1 to about 20 hours.

14. The process of claim 12 wherein the amine comprises a primary, secondary, or tertiary amine. $C_{1-20}$ aliphatic, $C_{2-20}$ alkoxy amine, hydroxyamine, the respective functionalized amines of the above, and mixtures thereof.

15. The process of claim 14 wherein the amine consists essentially of methylamine, ethyl amine, n-propylamine, n-butylamine, iso-butylamine, tertbutylamine, dimethyl amine diethylamine, di-n-propylamine, di-iso-propylamine, and dibutylamine, triethylamine and triethanolamine, hexamethylenetetramine, 2-ethylhexylamine, 2-aminopropanediol, hexylamine, ethanolamine, mixed $C_{20}$ amine, mixed $C_{10}$ amine, cyclohexylamine, 1,2 dimethoxypropane amine, triethylamine, ethanolamine, 1-amino-1,3-propanediol, 1-aminopentane, and 2-methyloxypropylamine.

16. The process of claim 12 wherein the amine is present in a concentration of from about 0.1 to about 1000 ppm.

17. The process of claim 16 wherein the amine is present in concentration of about 150 to about 400 ppm.

18. The process of claim 17 wherein the amine is present in concentration of about 200 to about 300 ppm.

19. The process of claim 12 wherein the aging step (c) is about 0.1–3 hours.

20. The process of claim 19 wherein the aging step is about 20–40 min.

21. The process of claim 20 wherein the aging step is about 20–30 min.

22. The process of claim 12 wherein the heating temperature of step (b) is about 80° C. to about 120° C.

23. The process of claim 22 wherein the heating temperature of step (b) is about 80° C. to about 100° C.

24. In a process for the manufacture of paraformaldehyde prills containing at least about 85% formaldehyde which comprises polymerizing the formaldehyde in the presence of an aqueous solution containing sodium hydroxide; extruding the polymerized formaldehyde through a nozzle to form prills which fall into a countercurrent flow of gas in a tower to further polymerize and solidify the product; collecting and removing the paraformaldehyde from the tower, the improvement comprising:
    a) providing a formaldehyde solution essentially absent of acid or basic catalyst and of a least 37% formaldehyde and contacting the formaldehyde solution with an amine stabilizer;
    b) heating the mixture of step (a) to a temperature ranging from about 70° C. to about 130° C.;
    c) aging the mixture for a sufficient amount of time to polymerize the formaldehyde mixture and form paraformaldehyde; and
    d) transferring the paraformaldehyde through a nozzle to form prills which fall into a countercurrent flow of gas in a tower to further polymerize and solidify.

25. In a process for the manufacture of paraformaldehyde prills containing at least about 85% formaldehyde which comprises polymerizing the formaldehyde in the presence of an aqueous solution containing sodium hydroxide; extruding the polymerized formaldehyde through a nozzle to form prills which fall into a countercurrent flow of gas in a tower to further polymerize and solidify the product; collecting and removing the paraformaldehyde from the tower, the improvement comprising:
    a) providing a formaldehyde solution of at least 37% formaldehyde;
    b) heating the mixture of step (a) to a temperature ranging from about 70° C. to about 130° C.;
    c) aging the mixture for a sufficient amount of time to polymerize the formaldehyde mixture and form paraformaldehyde;
    d) transferring the paraformaldehyde through a nozzle to form prills which fall into a countercurrent flow of gas in a tower to further polymerize and solidify;
    e) and contacting the paraformaldehyde prills by spraying with an amine stabilizer.

26. The process of claims 1, 12, 24, or 25 wherein the amine stabilizer is contacted with a $C_{1-20}$ aliphatic alcohol, $C_{5-15}$ aliphatic hydrocarbon, aromatic hydrocarbon, or a base additive.

27. The process of claim 26 wherein the additive is cyclohexane, acetone, methyl ethyl ketone, sodium hydroxide, ethanol, methanol, butanol, ethyl acetate, butyl acetate.

* * * * *